(12) United States Patent
Tuck et al.

(10) Patent No.: US 6,343,603 B1
(45) Date of Patent: Feb. 5, 2002

(54) CONNECTOR

(75) Inventors: Winton Charles Tuck; Brett John Huddart, both of Auckland (NZ)

(73) Assignee: Fisher & Paykel Limited, Auckland (NZ)

( * ) Notice: Subject to any disclaimer, the term of this patent is extended or adjusted under 35 U.S.C. 154(b) by 0 days.

(21) Appl. No.: 09/411,618

(22) Filed: Oct. 1, 1999

(30) Foreign Application Priority Data

Oct. 9, 1998 (NZ) .................................. 332268

(51) Int. Cl.$^7$ ............................................. A62B 18/10
(52) U.S. Cl. ............................ 128/205.24; 128/204.18; 128/207.12
(58) Field of Search .................. 128/204.18, 205.24, 128/204.26, 201.28, 203.11, 203.12, 203.16, 204.24; 137/614.06

(56) References Cited

U.S. PATENT DOCUMENTS

| | | | |
|---|---|---|---|
| 3,680,591 A | * | 8/1972 | Vik ........................ 137/614.05 |
| 4,324,239 A | | 4/1982 | Gordon et al. |
| 4,506,665 A | | 3/1985 | Andrews et al. |
| 4,812,083 A | * | 3/1989 | Mosier ........................ 405/186 |
| 5,365,973 A | * | 11/1994 | Fink, Jr. et al. ........ 137/614.04 |
| 5,398,673 A | * | 3/1995 | Lambert ................. 128/205.24 |
| 5,562,093 A | * | 10/1996 | Gerson ................... 128/205.24 |
| 5,813,401 A | * | 9/1998 | Radcliff et al. ........ 128/205.24 |
| 5,878,743 A | * | 3/1999 | Zdrojkowski et al. . 128/205.24 |
| 6,016,802 A | * | 1/2000 | Jackson .................. 128/205.25 |
| 6,056,010 A | * | 5/2000 | Wells ..................... 137/614.06 |

* cited by examiner

*Primary Examiner*—John G. Weiss
*Assistant Examiner*—V. Srivastava
(74) *Attorney, Agent, or Firm*—Trexler, Bushnell, Giangiorgi, Blackstone & Marr, Ltd.

(57) ABSTRACT

A connector has a main body with a breathing gases passageway extending therethrough. A connection at one end of the passageway is configured to engage with the expiratory tube connection of a ventilator. The other end of the passageway is connected to the expiratory arm of a breathing circuit. A flow restricting valve member is associated with the connection to the ventilator for substantially closing off the breathing gases passageway on disconnection of the connector from the ventilator.

4 Claims, 4 Drawing Sheets

CONNECTOR

BACKGROUND OF THE INVENTION

Field of the Invention

This invention relates to connectors, and in particular to connectors for connecting the expiratory tube of a breathing circuit to a ventilator.

A medical breathing circuit includes an inspiratory gases tube and an expiratory gases tube. The inspiratory tube has one end thereof connected to the patient, for example through an endotracheal breathing tube extending into the trachea and ending just above the lungs. The other end thereof connected to a ventilator. The connection to the ventilator may be direct or a self contained humidifier may be interposed. The expiratory tube is connected at one end to the end otracheal tube, and at the other end to the ventilator. The ventilator, running in "pressure support/control" or "volume support/control " modes, carefully controls the pressure of the gas supplied to the inspiratory tube to control the patient breathing, and maintains a positive airway pressure at all times to ensure lung inflation. An unfortunate consequence arises when the expiratory tube becomes detached from the ventilator, as the ventilator increases the supply flow rate in response to the sudden loss of pressure in the breathing circuit. The air supply becomes at once inefficient, and the increased turbulence of the higher flow level causes a more effective heat transfer from the heating system, and causes the inspiratory gases to be raised to a higher temperature than is otherwise desirable. Flow rates of about 0.5 to 10 liters per minute would be typical of such a circuit when used in a neonatal breathing circuit.

It is an object of the invention to provide a connector for the expiratovy tube of a breathing circuit which will obviate the above disadvantage or will at least provide healthcare providers with a useful choice.

In a first aspect, the invention includes a main body having a breathing gases passageway extending therethrough, connection means at one end of the passageway configured to engage with the expiratory tube connection of a ventilator, the other end of the passageway being connected or connectable to the expiratory tube of a breathing circuit, and flow restriction means associated with the connection means, for substantially closing off the breathing gases passageway upon disconnection of the connection means from the expiratory tube connection of a ventilator.

In a further aspect, the invention is a connector for series connection within the expiratory flow path of a breathing circuit. The connector includes a main body having a breathing gases passageway extending therethrough, connection means at one end of the passageway configured to engage with a connector of a subsequent component in the breathing circuit and the other end of the passageway being connected or connectable to a previous component in the breathing circuit; and flow restriction means associated with the connection means, for substantially but not completely closing off the breathing gases passageway upon disconnection of the connection means from the subsequent component connector.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the invention will now be described with reference to the accompanying drawings in which.

DETAILED DESCRIPTION OF THE PREFERRED EMBODIMENT

Figure 1:
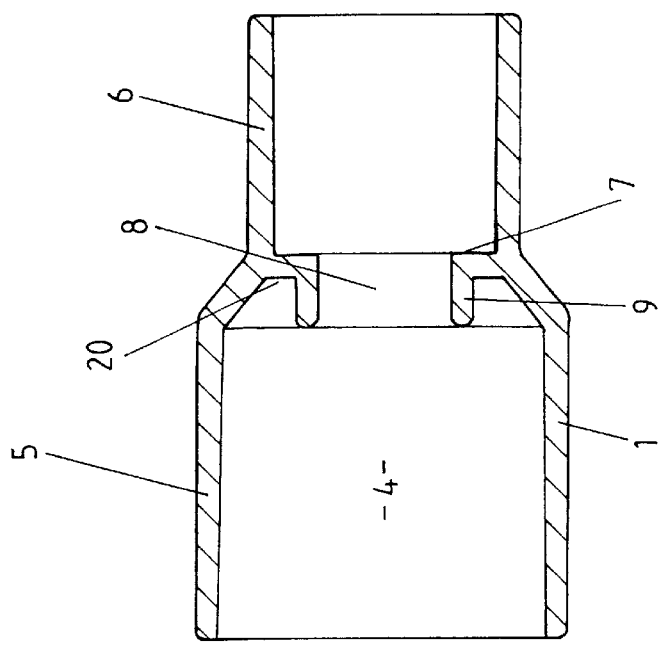
FIG. 1 is a side elevation assembly drawing in cross section through a connector according to the preferred embodiment of the present invention, showing the three components that fit together to form the connector.
Figure 1:
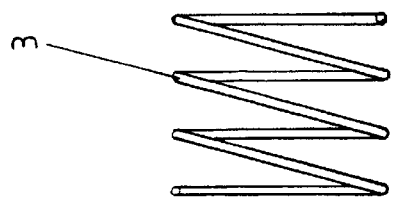
Figure 1:
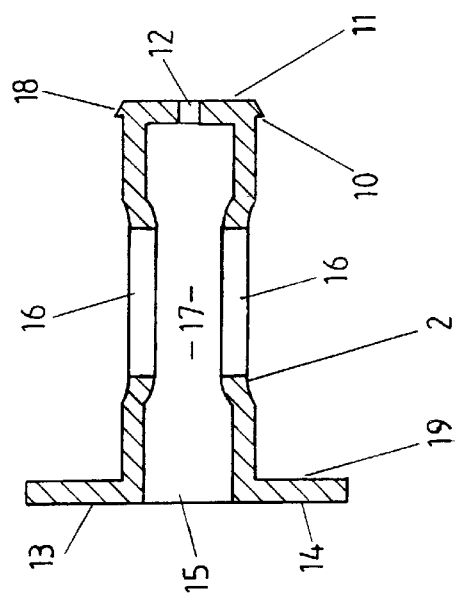
Figure 2:
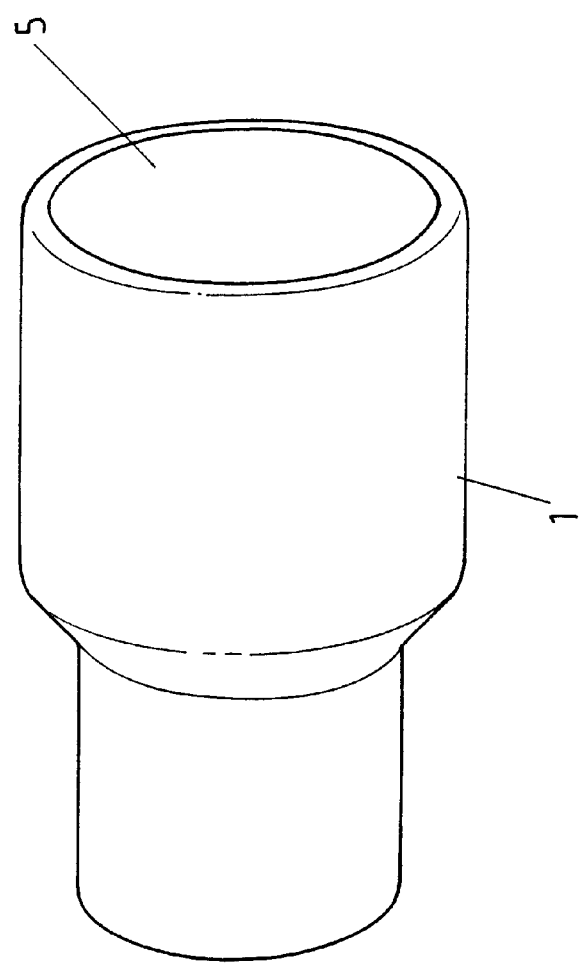
FIG. 2 is a perspective view assembly drawing to show the external appearance of the main connector body and the valve member.

The connector of the preferred embodiment of the present invention is shown in FIG. 1 in cross section. The connector broadly comprises assembly of three parts. A main connector body 1 with connections 5 and 6 for connecting it to the inlet connector and to the expiratory respiration tube respectively. In the preferred embodiment the connector main body is rotationally symmetric. The spring 3 fits within the open end 5 of the main body 1 which in use connects to the ventilator. One end of the spring 3 abuts an annular face 20 of a constriction within the connector main body, and is located and centered by an annular wall 9 which surrounds a passageway 8 passing through the constriction. A valve member 2 is the third main component, and passes through the passageway 8 so that end 11 thereof lies in the opening 6 of the connector on one side of the constriction and end 13 lies in opening 5 of the connector on the other side of the constriction, and tubular valve body 2 passes through the passageway 8. The spring 3 is effectively contained between the surface 19 of valve member 2 and the surface 20 of the constriction in the main body. The tubular valve body 2 has a small outwardly extending flange at the end 11 thereof, and under the action of the spring 3 the back face 10 of the flange abuts against the valve seat face 7 of the constriction of the connector main body 1 to retain the valve member 2 within the main body 1 and to form a substantial seal against gases passing therearound, the connector being that instance in the configuration shown in FIG. 4.

Figure 3:
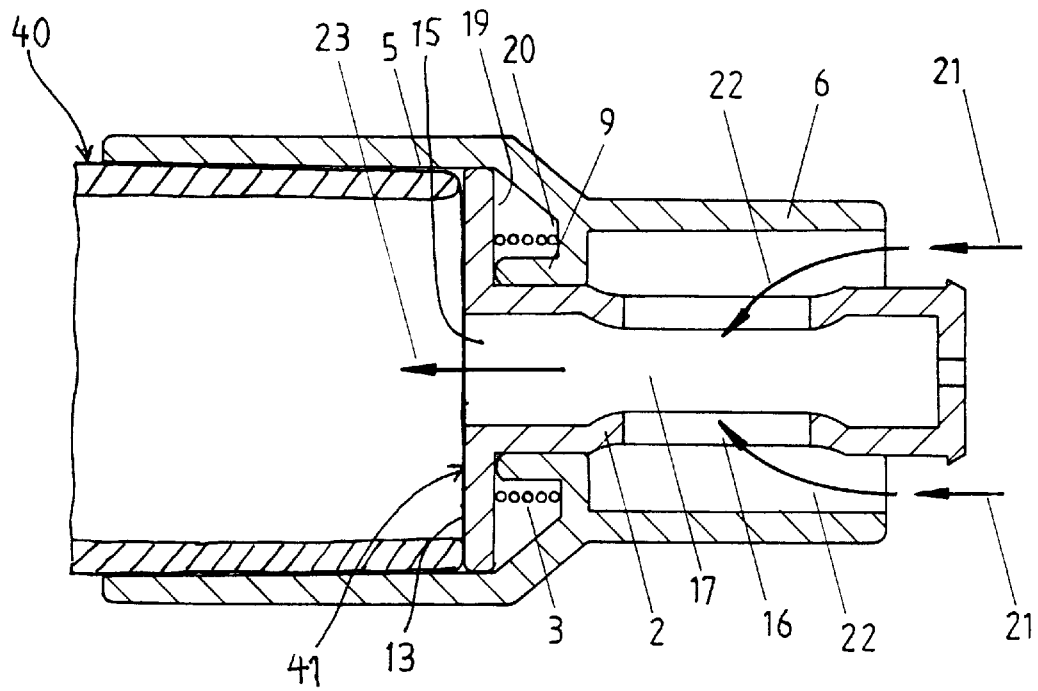
FIG. 3 is a side elevation in cross section of through the connector of the preferred embodiment of the invention with the valve in an open position, and showing the position of the ventilator connection in use.

Referring to FIG. 3 when the connector is fitted to the inlet fitting 40 of a ventilator the leading edge 41 of the fitting 40 presses against the outer face 14 of the valve member flange 13 to compress the spring 3 and open the valve. In its opened position airflow from the expiratory conduit can pass up the outsides of the valve member between the end 6 of the main body 1 and the tubular valve body 2 as indicated by arrows 21, through the ports 16 into the inside passage 17 of the tubular valve body 2 as indicated by arrows 22, out of the valve member 2 through outlet 15 into the ventilator end 5 of the connector main body 1 and thence to the ventilator. This flow path involves relatively large ports and passageways and does not provide a significant constraint against gas flow.

Figure 4:
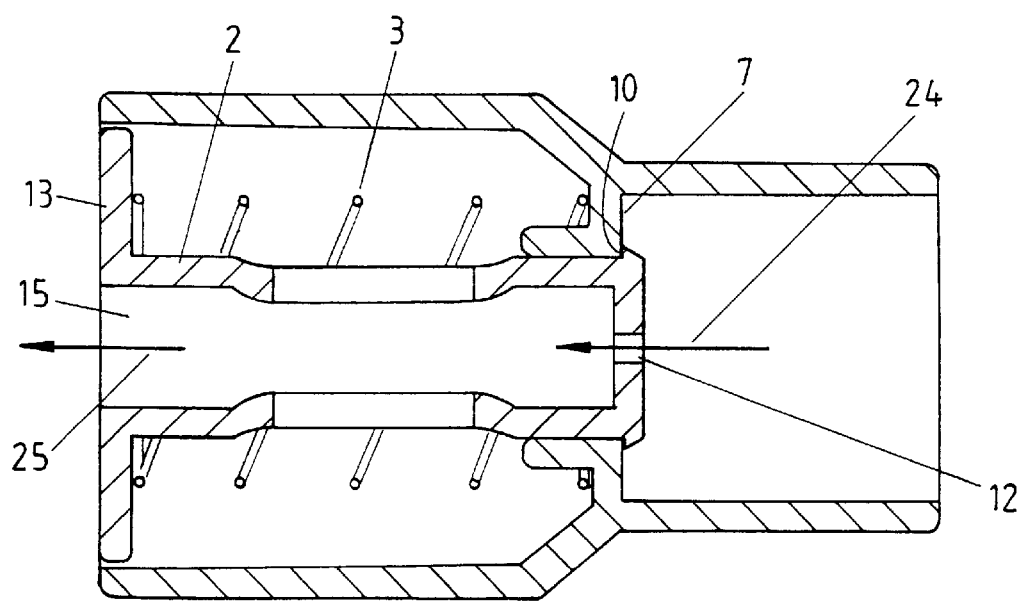
FIG. 4 is a side elevation in cross section of through the connector of the preferred embodiment of the invention with the valve in its closed position.

When, as shown in FIG. 4, the connector is not connected to the ventilator, the spring 3 pushes against the inside face 19 of the valve member end 13 so that the tubular valve body 2 is predominantly or exclusively contained within the ventilator side 5 of the connector main body 1, and the annular face 10 of the valve member seats against the annular face 7 of the constriction of the connector main body. To ensure that some gases may still flow through the breathing circuit a small aperture 12 is provided in the end 11 of the valve member so that gases may flow from the expiratory tube end 6 of the connector main body through the aperture 12 as indicated by arrow 24 and thereby into the tubular valve body 2 to be expelled through outlet 15 as indicated by arrow 25.

Each of the valve main body 1 and valve member 2 may be simply manufactured by injection moulding, for example a polyethylene plastics material or other suitable plastics material. The spring 3 may be of a standard spring material, A chamfer 18 on the leading face of end 11 of the valve member 2 allows easy assembly, essentially by a snap fit of the valve member 2 through the main passageway 8 of the main body 1.

Figure 5:
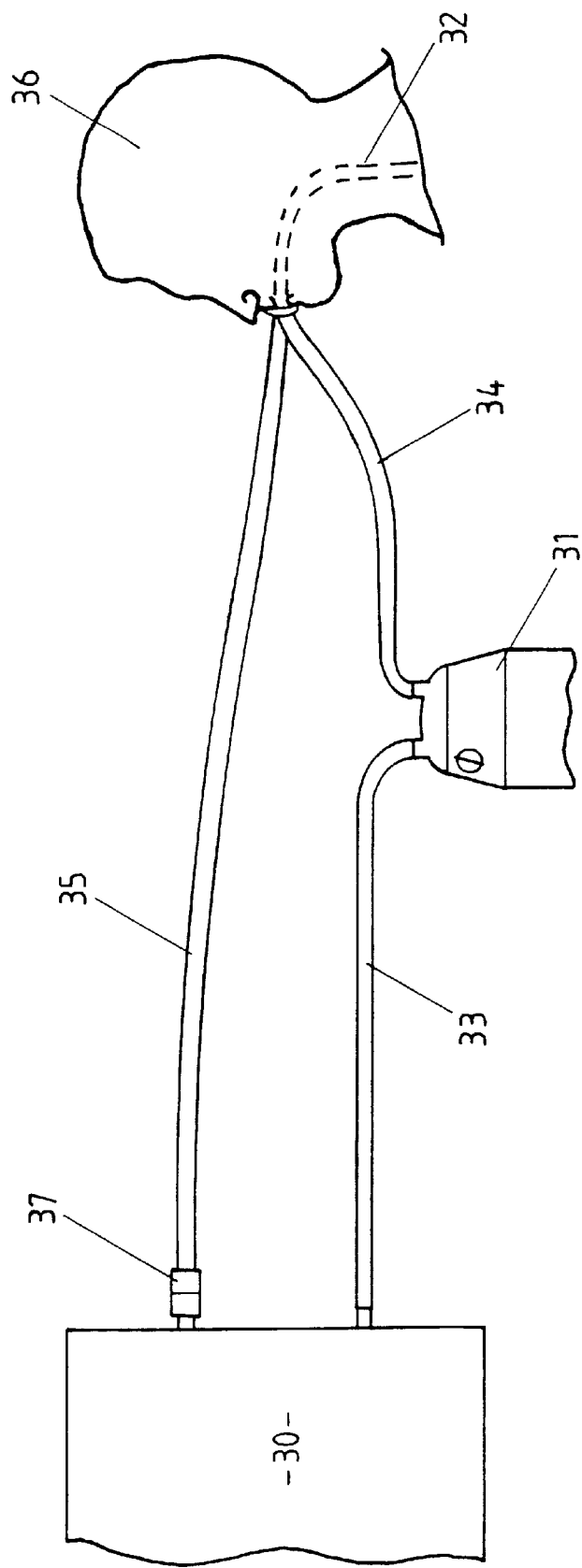
FIG. 5 is a diagram showing the breathing circuit, including ventilator, humidifier, endo tracheal tube (and patient), and the inspiratory and expiratory tubes.

The respiratory humidification circuit is shown diagrammatically in FIG. 5, and includes the ventilator 30, humidifier 31, endotracheal breathing tube 32 and the associated respiratory breathing tubes 33, 34 and 35. A patient 36 is shown. As indicated in FIG. 5 the connector of the present invention is used to connect between the expiratory breathing tube 35 and the inlet port of the ventilator 30 and is indicated by reference numeral 37. In normal use with the connector 37 properly connected to the inlet port of the ventilator 30 the connector provides a substantially unconstrained gases flow therethrough at normal ventilation flow levels of approximately 0.5 to 10 liters per minute for a neonatal breathing circuit, or 2 to 10 liters per minute for older patients. If the connector 37 should become detached from the ventilator 30 the valve member 2 will close, in the manner described above, and gases flow will be constrained to those losses arising at joints in the system, which are not significant, and that passing through the aperture 12 of the valve member 2 in the connector 37. This provides a substantial flow restriction so that the pressure in the breathing circuit is maintained at a sufficient level that the ventilator does not substantially increase the gases flow into the expiratory circuit tube.

What is claimed is:

1. A connector comprising:
    a main body having a breathing gases passageway extending therethrough, a section of said breathing gases passageway at one end adapted to fit, in use, tightly over an expiratory tube connection of a ventilator, the other end of said passageway being connected, or connectable in use, to an expiratory tube of a breathing circuit,
    a valve member including
        an abutment face at one end which will be born against by an expiratory tube connection of a ventilator to which said connector is connected in use, to move said valve member from a closed position to an open position,
        a central gases passage opening at one end through said abutment face and substantially closed at the other end,
        one or more gases ports in the wall of said central gases passage,
        means associated with said other end of said valve member which seat against an annular valve seat in said breathing gases passageway with said valve in said closed position, such that in said closed position said breathing gases passageway is at least substantially blocked by said seat and by said closed end, and in said open position gases may flow through said connector from said other end to said one end, and
        a bypass passageway of small flow capacity relative to a capacity of said breathing gases passageway, which bypass passageway allows a small level of flow through said valve member with said valve member in said closed position; and biasing means which biases said valve member toward said closed position.

2. A connector as claimed in claim 1 wherein said bypass passageway comprises an aperture in said closed end of said valve member central gases passage.

3. A connector for series connection within the expiratory flow path of a breathing circuit comprising:
    a main body having a breathing gases passageway extending therethrough, connection means at one end of said passageway configured to engage with a connector of a subsequent component in said breathing circuit and the other end of said passageway being connected or connectable to a previous component in said breathing circuit; and
    flow restriction means associated with said connection means, for substantially but not completely closing off said breathing gases passageway upon disconnection of said connection means from said subsequent component connector.

4. A connector as claimed in claim 3 wherein said flow restriction means comprises a valve member moveable between a closed position in which said gases passageway is substantially closed off, and an open position in which gases may pass freely in said gases passageway and biasing means which bias said valve member toward said closed position, said valve member including a bypass passage which is open, at least with said valve in said closed position, to allow a restricted flow through said breathing gases passageway.

* * * * *